US008828322B2

(12) United States Patent
Chen et al.

(10) Patent No.: US 8,828,322 B2
(45) Date of Patent: Sep. 9, 2014

(54) DEVICE AND METHOD FOR MEASURING PROTHROMBIN TIME AND HEMATOCRIT BY ANALYZING CHANGE IN REACTANCE IN A SAMPLE

(75) Inventors: Sz-Hau Chen, Hsinchu (TW); Yueh-Hui Lin, Hsinchu (TW); Ching-Yuan Chu, Hsinchu (TW); Chu-Ming Cheng, Hsinchu (TW); Guan-Ting Chen, Hsinchu (TW); Yi-Chen Lu, Hsinchu (TW); Thomas Y.S. Shen, Hsinchu (TW)

(73) Assignee: Apex Biotechnology Corp., Hsinchu (TW)

( * ) Notice: Subject to any disclaimer, the term of this patent is extended or adjusted under 35 U.S.C. 154(b) by 104 days.

(21) Appl. No.: 13/156,693

(22) Filed: Jun. 9, 2011

(65) Prior Publication Data
US 2011/0303556 A1 Dec. 15, 2011

Related U.S. Application Data

(60) Provisional application No. 61/353,137, filed on Jun. 9, 2010.

(51) Int. Cl.
*G01N 15/06* (2006.01)
(52) U.S. Cl.
USPC .......... 422/82.01; 422/50; 422/68.1; 422/502; 422/503; 436/43; 436/63; 436/66; 436/149
(58) Field of Classification Search
USPC .......... 422/50, 68.1, 502, 503, 82.01; 436/43, 436/63, 66
See application file for complete search history.

(56) References Cited

U.S. PATENT DOCUMENTS

| | | | |
|---|---|---|---|
| 3,699,437 | A | 10/1972 | Ur |
| 4,547,735 | A | 10/1985 | Kiesewetter et al. |
| 5,144,240 | A | 9/1992 | Mehdizadeh et al. |
| 5,418,141 | A * | 5/1995 | Zweig et al. ............. 435/13 |
| 6,046,051 | A | 4/2000 | Jina |
| 6,060,323 | A | 5/2000 | Jina |
| 6,066,504 | A | 5/2000 | Jina |
| 6,338,821 | B1 | 1/2002 | Jina |

(Continued)

FOREIGN PATENT DOCUMENTS

| | | |
|---|---|---|
| CN | 1491358 A | 4/2004 |
| JP | 05-007564 | 1/1993 |

(Continued)

OTHER PUBLICATIONS

Japanese Patent Application No. 2001-129559; Japanese Office Action dated Sep. 21, 2012 with English translation thereof.

(Continued)

*Primary Examiner* — Brian J Sines
(74) *Attorney, Agent, or Firm* — Morgan, Lewis & Bockius LLP

(57) ABSTRACT

Devices and methods for measuring prothrombin time (PT) and hematocrit (HCT) by analyzing the change in reactance in a sample are presented. A diagnostic device for measuring HCT and PT of a fluid includes a relative electrode-type sensor device and a blood test card assembly including one or more pairs of electrodes, wherein alternating current (AC) provided by the sensor device is used to measure and calculate HCT and PT of blood test using the reactance analysis.

8 Claims, 14 Drawing Sheets

(56) References Cited

U.S. PATENT DOCUMENTS

| | | | |
|---|---|---|---|
| 6,673,622 B1* | 1/2004 | Jina | 436/69 |
| 7,005,857 B2 | 2/2006 | Stiene et al. | |
| 2003/0146113 A1 | 8/2003 | Unkrig et al. | |
| 2008/0224716 A1 | 9/2008 | Singer et al. | |
| 2009/0118666 A1* | 5/2009 | Blomqvist et al. | 604/66 |
| 2009/0205399 A1 | 8/2009 | Sun et al. | |

FOREIGN PATENT DOCUMENTS

| | | |
|---|---|---|
| JP | 2003-524184 A | 8/2003 |
| JP | 2007-537205 A | 12/2007 |
| JP | 2008-545952 A | 12/2008 |
| JP | 2009-518151 A | 5/2009 |
| WO | WO 01/63271 A1 | 8/2001 |
| WO | WO02/50534 A1 | 6/2002 |
| WO | WO 2005/107795 A1 | 11/2005 |
| WO | WO 2006/122554 A2 | 11/2006 |
| WO | WO 2007/067941 A2 | 6/2007 |
| WO | 2007/075410 A2 | 7/2007 |

OTHER PUBLICATIONS

Cha et al. (1994) An electronic method for rapid measurement of haematocrit in blood samples, Physiol. Meas., 15:129-137.

Chen (Jun. 2005) Electric impedance and coagulation time measurement of human whole blood, Institute of Micro-Electro-Mechanical System, National Cheng Kung University, Tainan, Taiwan, R.O.C.

European Search Report dated Nov. 3, 2011, European Patent Application 11169337.0.

* cited by examiner

| Hematocrite(%) | Reactance(ohm) | variation |
|---|---|---|
| 29 | 620.29 | 0.37 |
| 39 | 652.17 | 4.21 |
| 47 | 676.59 | 2.80 |

| coagulation time(sec) | reactance change rate | variation |
|---|---|---|
| 9.8 | 0.10 | 0.01 |
| 21.7 | -0.18 | 0.01 |
| 32.8 | -0.49 | 0.02 |

| coagulation time (sec) | calculated PT by impedance (sec) | variation |
|---|---|---|
| 9.8 | 8.2 | 3.7 |
| 21.7 | 25.1 | 2.4 |
| 32.8 | 31.0 | 2.4 |

| coagulation time (sec) | calculated PT by reactance (sec) | variation |
|---|---|---|
| 9.8 | 10.1 | 0.2 |
| 21.7 | 21.2 | 0.5 |
| 32.8 | 33.1 | 0.9 |

DEVICE AND METHOD FOR MEASURING PROTHROMBIN TIME AND HEMATOCRIT BY ANALYZING CHANGE IN REACTANCE IN A SAMPLE

CROSS REFERENCE TO RELATED APPLICATIONS

This application is based upon and claims the benefit of priority from U.S. Provisional Application No. 61/353,137, filed on Jun. 9, 2010, the entire contents of which are incorporated herein by reference.

FIELD OF THE INVENTION

The present invention relates to biochemical diagnostic devices, and more particularly, to devices and methods for determining hematocrit (HCT) and prothrombin time (PT) by analyzing a change in reactance in a sample.

BACKGROUND OF THE INVENTION

Two pathways or coagulation cascades, known as the intrinsic and extrinsic pathways, lead to the formation of a clot in blood. When a human body is injured, the extrinsic pathway is first triggered to control the body's blood coagulation. In addition to a blood sample, the coagulation reaction needs some additional tissue factors. The inactive factor X is catalyzed into factor Xa. The prothrombin (factor II) can be transformed from the factor Xa to the thrombin (factor IIa) by the effects of factor Va, acidic phospholipids and calcium ions. The thrombin then transforms fibrinogen into fibrin, enhancing the platelet of the endothelial cells gathered at the injury. The thrombin can also enhance the role of factor XIII, linking each fibrous protein molecule to a stable fibrin. Therefore, inspecting the prothrombin time not only allows determining whether the function of external activation factors of the coagulation system are normal, but also allows assessing and monitoring oral anticoagulants treatment, liver function, vitamin K deficiency, coagulation factor deficiency, and disseminated intravascular coagulation (DIC) syndrome.

Conventional inspection methods for measuring the prothrombin time analyze the condensation phenomenon of transforming the serum soluble protein into an insoluble protein during blood coagulation. These inspection methods can be realized by detecting optical characteristics, such as changes in color, reflection, refraction, luminescence and fluorescence. Such inspection methods, however, require a substantial number of blood test samples and high purity reagents and are time-consuming, as disclosed in U.S. Pat. No. 5,418,141, the entirety of which is hereby incorporated by reference. Moreover, these inspection methods require long detection times and a significant amount of supplies, resulting in inconvenience and higher costs.

Other conventional inspection methods for measurement of the prothrombin time use electrochemical inspection methods. For example, U.S. Pat. No. 3,699,437, the entirety of which is hereby incorporated by reference, discloses observing the comparative decline rate of resistance from the initial to the lowest point. The calculated result is served as a basis for determining coagulation time in which the impedance measurement is related to the mechanism of blood coagulation. Further, U.S. Pat. Nos. 6,060,323; 6,338,821; 6,066,504; 6,673,622; and 6,046,051, the entirety of each of which is hereby incorporated by reference, disclose electronic sensor devices and a test card assembly for the measurement of the coagulation time of a blood sample. The test card assembly is designed with a single electrode or a plurality of electrodes according to the measurement demands of the device. The sample is contacted with the electrodes, which measure the change in impedance corresponding to the change of viscosity of the blood sample as it coagulates. This technique, however, may result in test errors due to the hematocrit and the electrolyte concentration differences among blood test samples in individuals. U.S. Pat. No. 7,005,857, the entirety of which is hereby incorporated by reference, discloses a coagulation inspection device with automatic collection of blood samples. The coagulation inspection device determines the coagulation time by measuring capacitance or impedance changes between two electrodes. These technologies may, therefore, improve the simplicity of the detection device, but they cannot achieve the relatively higher precision and accuracy that the above-discussed optical detection methods may achieve.

Accordingly, a new biosensor device is needed and described herein for measuring prothrombin time (PT) and hematocrit (HCT), one capable of operating with short test times, simple procedures for the user and while achieving highly accurate results.

SUMMARY OF THE INVENTION

One aspect of the present invention is to use reactance measurements taken from a sample to calculate prothrombin time (PT). As described herein, using reactance measurements as opposed to impedance measurements provides a more accurate analysis of the blood's characteristics, reduces the chance of a test error, and improves measurement accuracy.

Another aspect of the present invention is to provide a detection system and a measurement method for determining prothrombin time (PT) and hematocrit (HCT) of a blood sample using a reactance analysis of the sample. In one embodiment, the detection system includes a sensor device and a test card assembly. The test card assembly includes one or more pairs of the carbon or precious metal electrodes, set on the same plane or on different planes, respectively. Alternating current (AC) provided by the sensor device is used to measure reactance and calculate the PT and HCT of the blood sample using the reactance analysis described herein.

Another aspect of the invention is to provide a test card assembly with an improved blood sample and reagent contact area. The test card assembly according to some embodiments of the present invention utilizes porous materials, such as fiberglass substrate (FR-4), for at least a portion of a substrate of the test card. Since the surface of at least a portion of the substrate, preferably the majority of the surface of the substrate that comes in contact with the sample, is porous, e.g., it may have a plurality of holes, voids, or cavities thereon, the sample (e.g., blood) is improvably, uniformly dispersed on the substrate, thereby increasing the contact area of the blood sample and reagents, and effectively improving on drawbacks of traditional non-porous materials used for substrates. According to the present invention, the problems associated with having a relatively poor contact between the sample and the reagent that occur when using non-porous materials for the substrate, or a portion thereof, e.g., relatively high blood cohesion, are minimized or eliminated.

According to one aspect of the invention, a diagnostic device for measuring PT and HCT of a fluid includes: a electrode-type sensor device; and a blood test card assembly including one or more pairs of electrodes, wherein alternating current (AC) provided by the sensor device is used to measure and calculate prothrombin time and HCT of the blood test using the reactance analysis described herein.

In one embodiment, the sensor device includes: a test card receiving unit for accommodating the test card assembly; a temperature maintaining unit for controlling and maintaining temperature of the test card receiving unit at a constant temperature; an AC generation unit for providing an alternating current with predetermined frequency and voltage to the test card assembly; a signal receiving unit to receive a response signal from the test card assembly; a microprocessor for calculating the response signal and rendering results of the HCT and the prothrombin time; and a display unit for displaying inspected results of the HCT and the prothrombin time from the microprocessor.

According to another aspect of the invention, a diagnostic device for measuring HCT and/or PT of a sample includes: an electrode-type sensor device; a test card assembly including one or more pairs of electrodes; a power source for providing an AC test signal at a constant frequency to electrodes of the test card assembly; a signal retrieving unit coupled to the test card assembly; a phase angle calculating unit; a microprocessor in the sensor device programmed for analyzing a response signal from the test card assembly, an output from the phase angle calculating unit and performing a reactance analysis of a sample provided on the test card assembly; and a display for displaying PT and/or HCT of the sample.

According to another aspect of the invention, a method for measuring HCT and/or PT of a sample includes: providing a test card assembly to a test card receiving unit; controlling and maintaining temperature of the test card receiving unit at a constant temperature; providing a sample to be inspected to the test card assembly; providing an alternating current with predetermined frequency and voltage to the test card assembly by an AC generation unit; receiving a response signal from the test card assembly and calculating the HCT and/or PT by a microprocessor; and providing an inspected result to a display unit.

According to an additional aspect of the invention, a method for measuring HCT and/or PT of a sample includes: providing a test card assembly to a test card receiving unit; providing a sample to be inspected to the test card assembly; providing an alternating current with predetermined frequency and voltage to the test card assembly by an AC generation unit; receiving a response signal from the test card assembly; performing a reactance analysis of the sample; and determining the HCT or the prothrombin time with a microprocessor; and providing an inspected result to a display unit.

According to yet another aspect of the invention, a method for measuring HCT and/or PT of a sample includes: coupling a test card having a substantially porous surface on the substrate at a sample region of the test card to a sensor unit programmed to measure HCT and/or PT of a blood sample; providing a blood sample to be analyzed to the test card sample region; providing an alternating current with a predetermined frequency and voltage to the test card; sensing a response signal from the sample on the test card; performing a reactance analysis of the sample; determining a phase change related to the capacitance in the blood sample using a microprocessor programmed to determine the phase change caused due to reactance in the blood sample; and determining the HCT and/or PT of the bloods sample with the microprocessor; and providing an inspected result to a display unit of the sensor unit.

BRIEF DESCRIPTION OF THE FIGURES AND PICTURES

The foregoing aspects and many of the attendant advantages of this invention will become more readily appreciated by reference to the following detailed description, when taken in conjunction with the accompanying pictures, wherein.

Figure 9:
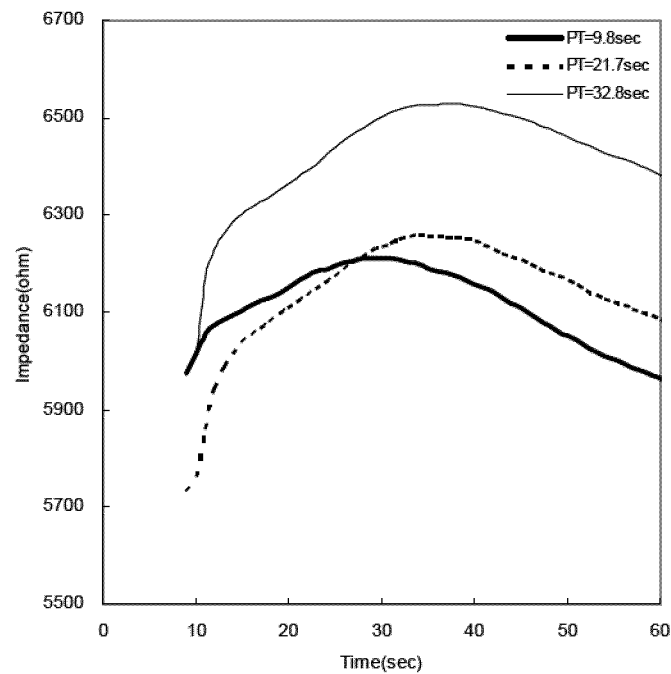
Figure 10:
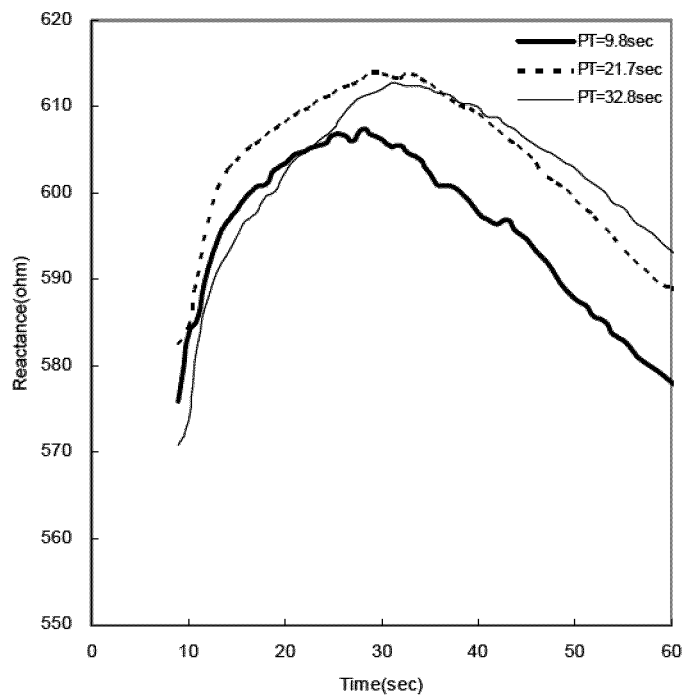
Figure 11:
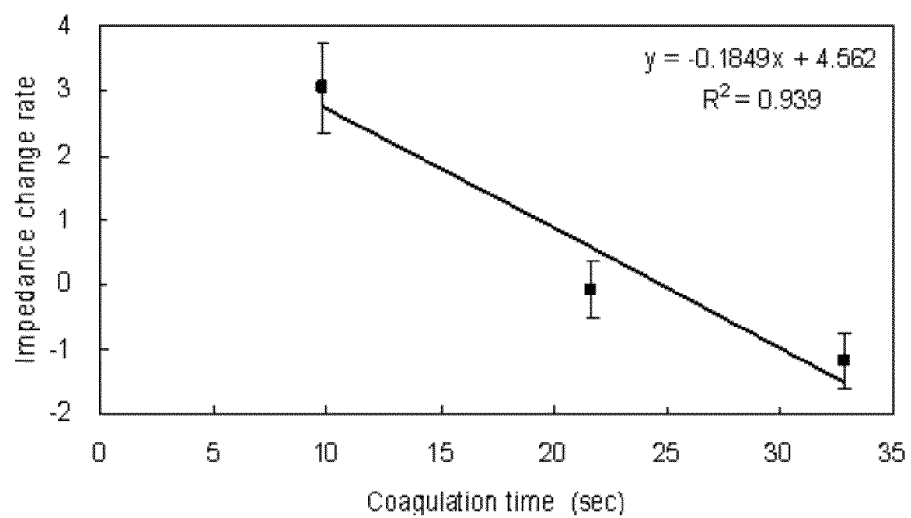
Figure 12:
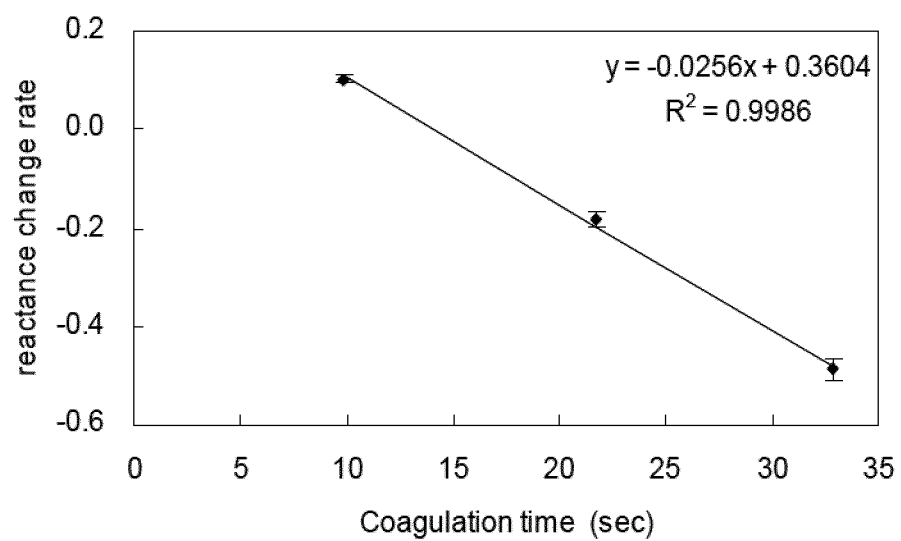
Figure 13:
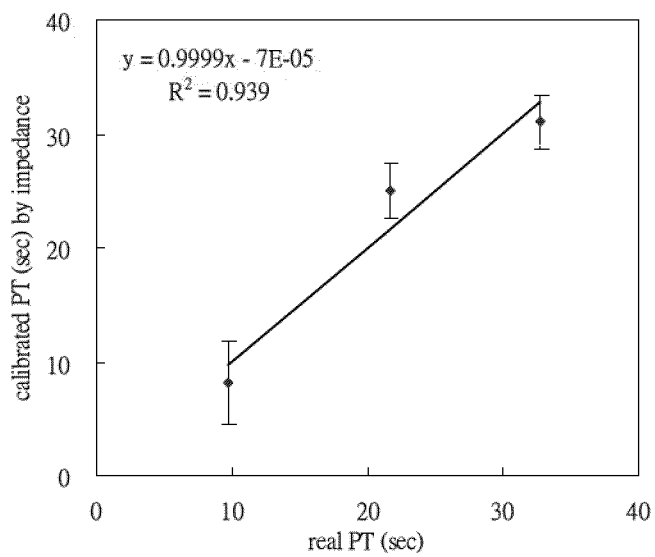
Figure 14:
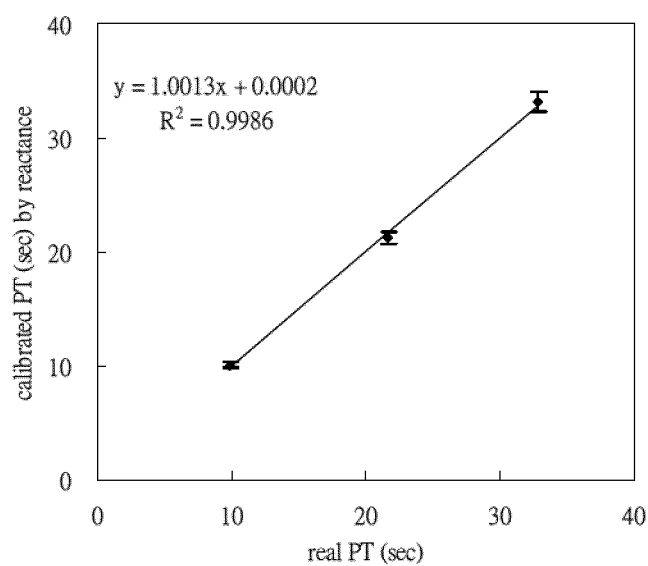
Figure 15A:
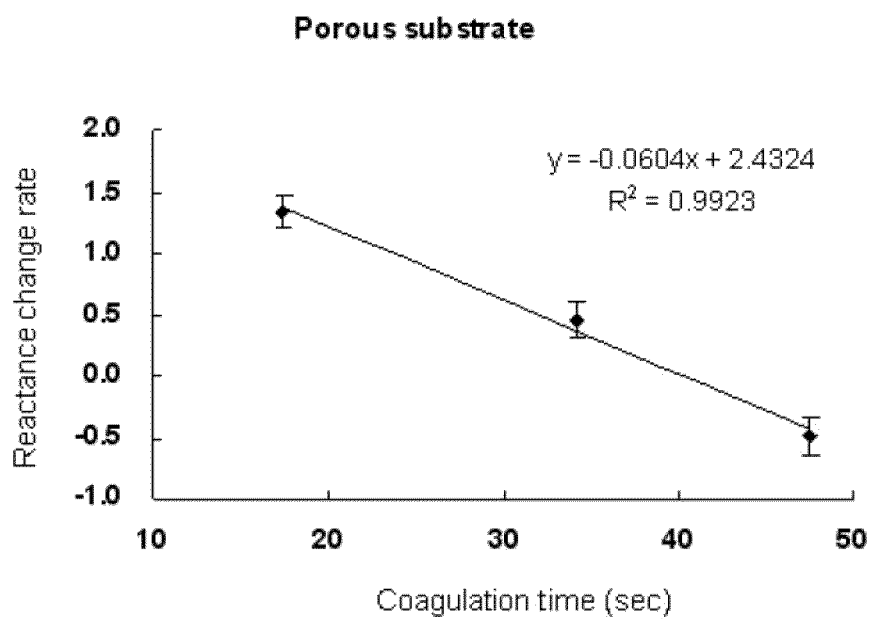
Figure 15B:
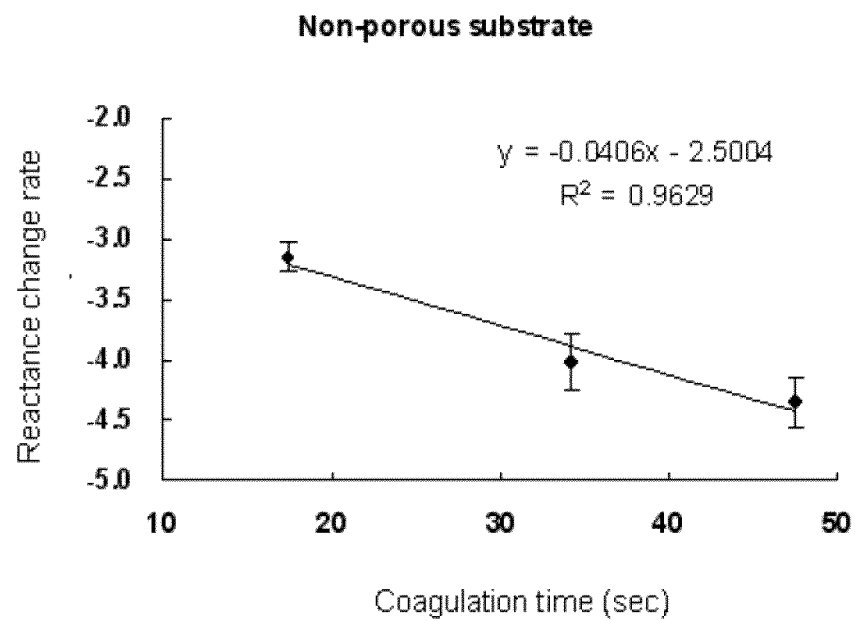
Figure 16A:
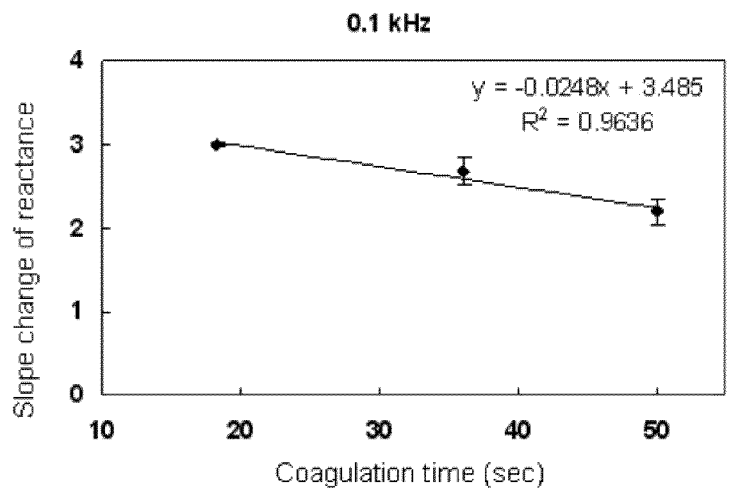
Figure 16B:
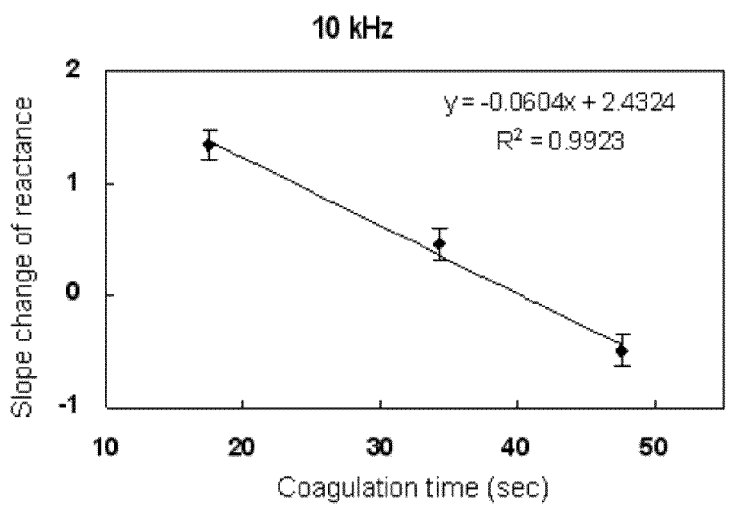
Figure 16C:
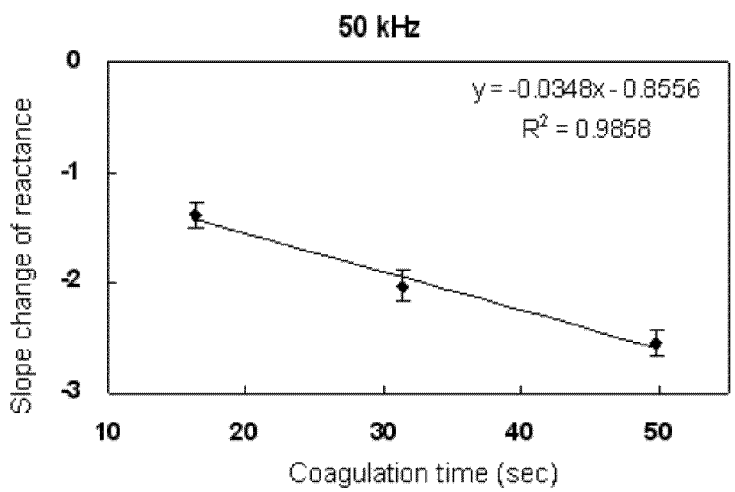

FIGS. 9 and 10 depict exemplary impedance and reactance values measured by an LCR meter every 0.5 second over 60 seconds;

FIGS. 11 and 12 depict exemplary PT vs. impedance change rate calibration curve and PT vs. reactance change rate calibration curve, respectively;

FIGS. 13 and 14 depict exemplary graphs of Calibrated PT vs. Real PT by impedance and Calibrated PT vs. Real PT by reactance, respectively;

FIGS. 15A and 15B are experimental graphs showing the blood coagulation analyses using a porous substrate and a non-porous substrate, respectively; and FIGS. 16A-16C are experimental graphs showing blood coagulation analyses at different frequencies using the reactance methods of measurement according to the present invention.

DETAILED DESCRIPTION OF THE INVENTION

Reference will now be made in detail to several exemplary embodiments of the invention, examples of which are illustrated in the accompanying drawings and photographs. Wherever possible, the same reference numbers are used in the drawings and the description to refer to the same or like parts. In the drawings, the shape and thickness of an embodiment may be exaggerated for clarity and convenience. This description will be directed in particular to elements forming part of, or cooperating more directly with, apparatus in accordance with the present invention. It is to be understood that elements not specifically shown or described may take various forms well known to those skilled in the art. Further, when a layer is referred to as being on another layer or "on" a substrate, it may be directly on the other layer or on the substrate, or intervening layers may also be presented.

Some exemplary embodiments of the present invention are described in greater detail by referring to the drawings and photographs that accompany the present application. It should be noted that the features illustrated in the drawings are not necessarily drawn to scale. Descriptions of well-known components, materials, and process techniques may be omitted so as to not unnecessarily obscure the embodiments of the invention. Any devices, components, materials, and steps described in the embodiments are only for illustration and not intended to limit the scope of the present invention.

In view of the aforementioned problems noted of the conventional technologies, the following embodiments provide a system and methods for determining hematocrit (HCT) and prothrombin time (PT) of a sample (for example, a blood sample) by performing a reactance analysis on the sample, also referred to as a reactance measurement module. Measurements for blood coagulation, or HCT, by performing a reactance analysis as disclosed herein may be suitably used in quantitative analysis of prothrombin time (i.e., clotting time). As used herein, the term "hematocrit" refers to the percentage of packed red blood cells in a volume of whole blood.

One exemplary embodiment of the invention provides an electrode-type sensor device with a sample test card including one or more pairs of electrodes. The base plate of the test card may be made of porous materials or non-porous materials, but preferably the substrate is made of porous materials as described and shown herein. The electrodes may be made of carbon or other conductive materials, but preferably are made of precious metals which include, for example, gold, silver, palladium, platinum, nickel, alloys thereof, and combinations thereof known to those skilled in the art. In one aspect of the invention, an alternating current (AC) module or an AC/DC power source provides a test signal to the blood test card with an oscillated frequency in a range between about 0.1 KHz and about 50 KHz. The amplitude of voltage applied to the test card is in a range of about 0.05 V to about 5 V. The signal is applied to the test card to measure the reactance of the sample. As used herein in connection with a measured quantity, the term "about" refers to that variation in the measured quantity as would be expected by the skilled artisan performing the measurement and exercising a level of care commensurate with the objective of the measurement and the precision of the measuring apparatus being used.

In one preferred aspect of the invention, as blood coagulation in a sample caused by enzymatic reactions proceeds, the responding signals are received and processed by the sensor device according to the slope differences depending on the prothrombin time periods analyzed by the reactance measurement. In one embodiment, the electrodes may be gold electrodes. In one example, an AC module is adopted for taking a reactance measurement of the sample according to the responding oscillated test signal sensed from the blood test card, wherein as the blood coagulation caused by the enzyme reactions proceeds the resultant signals are received and processed by the sensor device according to the slope differences depending on the prothrombin time periods analyzed by the reactance measurement.

Principles of performing a reactance analysis according to embodiments of the present invention are discussed below. The impedance of an AC circuit equals the sum of resistance (R) and the product of reactance (X) and the phase angle θ:

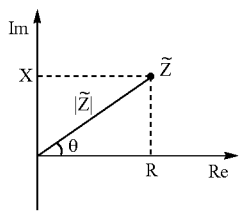

wherein reactance (X) is the imaginary part of the complex quantity, impedance (Z), representing the obstacles to the current flow created by a combination of inductances (L) and capacitances (C). Resistance (R) is the real part of the complex quantity. As known to those skilled in the art, the reactance changes with changes in the frequency, changes in the capacitance and/or changes in the inductance of the AC circuit. When the reactance of the AC circuit changes, there will be a phase change between the circuit's current waveform and voltage waveform. The impedance (Z) is defined as:

$$Z=R+jX, \text{ and } |Z|=(R^2+X^2)^{1/2} \qquad (1)$$

where Z is impedance, R is resistance, j is phase, and X is reactance; and $$X=X_C+X_L, X_L=2\pi f L, \text{ and } X_C=1/2\pi f C \qquad (2)$$

where $X_C$ is capacitance reactance, $X_L$ is inductance reactance, π is a ratio of the circumference of a circle to its diameter, f is frequency, L is inductance, and C is capacitance.

In one aspect of the invention, an AC generation unit of the detection system provides an AC test signal to the test card. A sample is applied to the test card in a sample test area of the test card. As the sample between the electrodes is charged, the induced charges are polarized in the electric field to form capacitances and the sample reacts somewhat like a capacitor. As a blood sample clots, during the clotting a media forms between the electrodes, impeding movement of charges in the sample such that charges accumulate on the electrodes. The accumulated charges thereby cause a capacitance to develop. In a preferred aspect of the invention, since the frequency (f) of the AC generation unit of the detection system remains constant, the inductance (L) and the inductance reactance $(X_L)$ is also constant, and, therefore, the variation in the capacitance reactance in the sample equals essentially the variation in the overall reactance as shown by the following equation:

$$X_{C2}-X_{C1}=X_2-X_1 \qquad (3)$$

where $X_{C2}-X_{C1}$ is the variation in the capacitance reactance, and $X_2-X_1$ is the variation in the reactance.

By determining reactance variation of the sample per unit time, the capacitance reactance variation per unit time and the capacitance variation per unit time during characteristics of the blood clotting in the sample can be determined. Prothrombin time (i.e., clotting time) measurement may thus be determined accurately by performing a slope calculation with the help of the reactance measurement module of the invention.

Figure 1:
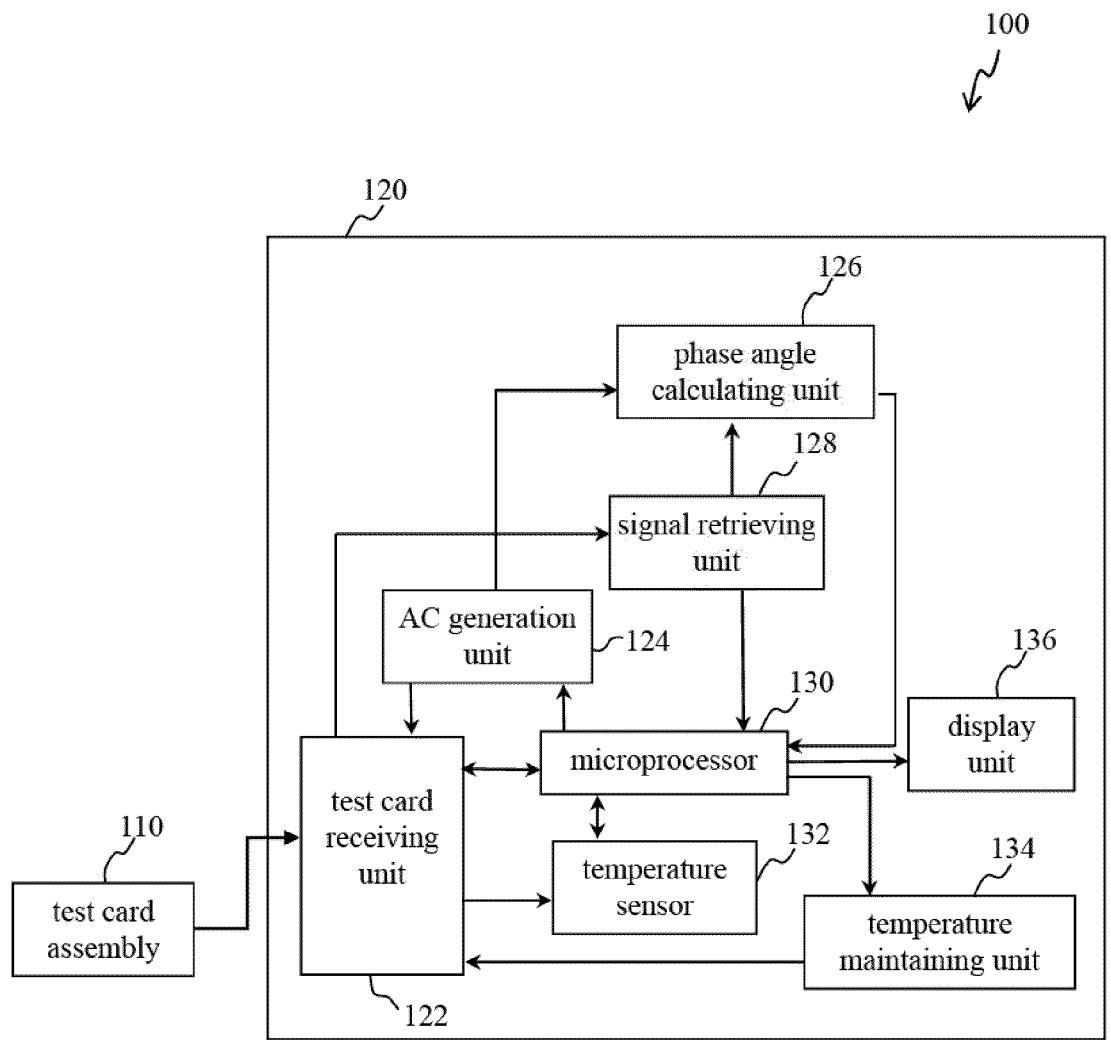
FIG. 1 is a schematic view of an exemplary diagnostic device for measuring HCT and/or PT in accordance with embodiments of the present invention.

FIG. 1 is a schematic view of an exemplary diagnostic device for measuring prothrombin time and/or HCT in accordance with embodiments of the present invention. As illustrated in FIG. 1, a diagnostic device 100 for measuring prothrombin time and/or HCT of a fluid includes a relative electrode-type sensor device 120 and a sample test card assembly 110 including one or more pairs of electrodes, wherein alternating current (AC) provided by the sensor device is used to measure and calculate prothrombin time and HCT of blood test using the reactance analysis. In this embodiment, the sensor device 120 includes a test card receiving unit 122 for accommodating the test card assembly 110. A temperature maintaining unit 134 is used for controlling and maintaining temperature of the test card receiving unit at a constant temperature. An AC generation unit 124 provides an alternating current with predetermined frequency and voltage to the test card assembly 110. A signal retrieving unit 128 is used to retrieve a response signal from the test card assembly. A microprocessor 130 is used for analyzing the response signal and rendering results of the HCT and/or the prothrombin time. A display unit 136 is used for displaying inspected results of the HCT and/or the prothrombin time from the microprocessor 130.

Figure 2:
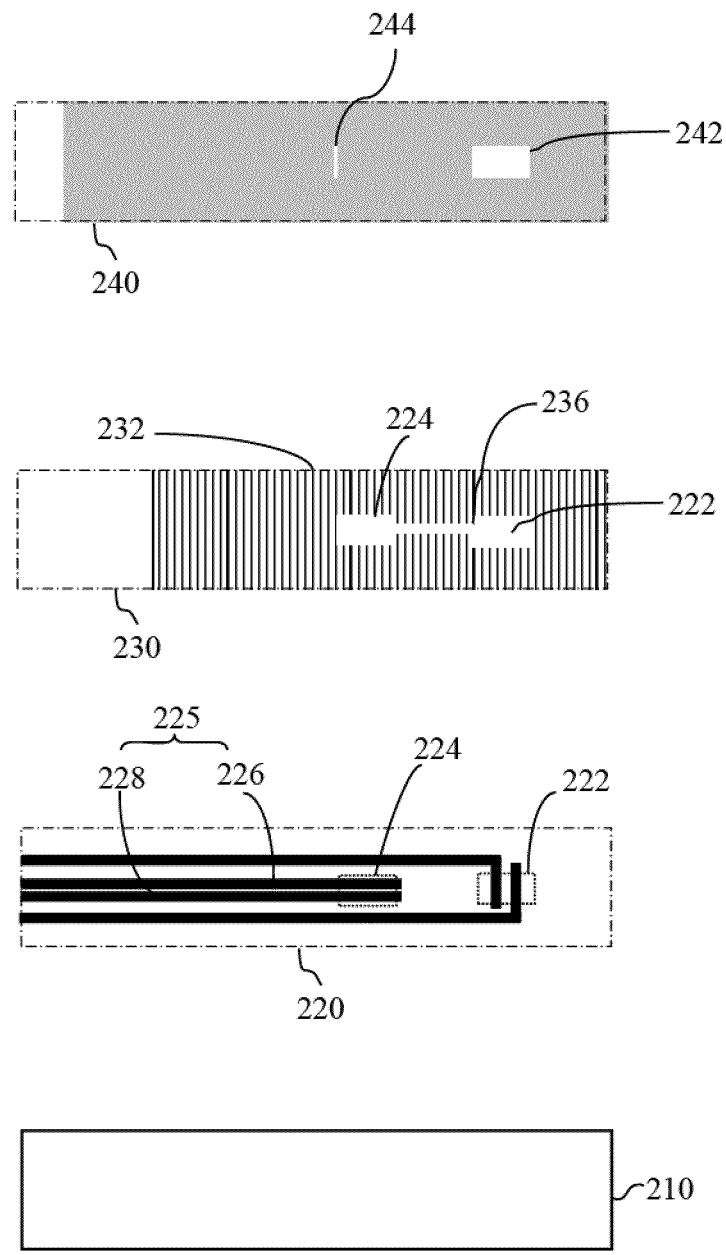
FIG. 2 illustrates an explosive view of a blood test card in accordance with one embodiment of the present invention wherein the broken line indicates the relative positions between various elements.

FIG. 2 illustrates an explosive view of a sample test card for a sample in accordance with one embodiment of the present invention wherein the broken line indicates the relative positions between various elements. The sample test card includes an insulating substrate 210, an electrode system 220, a separation and reaction layer 230 and a cover 240. The insulating substrate 210 is electrically insulating, and its material may include, but is not limited to, a base plate composed of porous materials. In preferred embodiments of the invention, the base plate of the test card assembly includes pores, cavities, voids or holes with diameters in a range of about 0.1 µm to about 10 µm, about 0.01 µm to about 100 µm, about 0.1 µm to about 50 µm, about 0.1 µm to about 20 µm, about 0.1 µm to about 5 µm, or about 5 µm to about 10 µm. The electrode system 220 may be made with any conductive materials, including but not limited to carbon, gold, silver, copper, carbon silver, palladium, nickel, and other similar materials and combinations thereof according to the invention. The electrode system 220 includes one or more pairs of the noble metal electrodes, set on the same plane or on different planes respectively. For example, a set of testing electrodes 225 includes a pair of electrodes 226 and 228. According to the principles of the invention, the electrode structure is not limited to specific arrangements of the set of testing electrodes 225 as shown or the exact number of electrodes as shown. Additional electrodes may be provided according to different application needs. The electrode system further electrically connects the electrode system with a measurement device (not shown).

The separation layer 230 is depicted as including spacers 232 disposed over the electrode system 220. The separation layer 230 further may include a reaction region 224 to expose a part of the reagent (not shown) and a sampling region 222. A channel 236 may connect the sampling region 222 and reaction region 224. The size of the reaction region 224 is preferably sufficient to expose part of the electrodes 226 and 228. In this example, the reaction region 224 is used for measurement of the prothrombin time, and the sampling region 222 may be used for measurement of the HCT.

The cover 240 is disposed on the separation layer 230. In one embodiment, the cover 240 includes an inlet 242 and a gas vent 244, which are respectively connected to the sampling region 222 and the reacting region 224. The size of the sampling space depends upon the thicknesses of the separation layer 230.

Figure 3A:
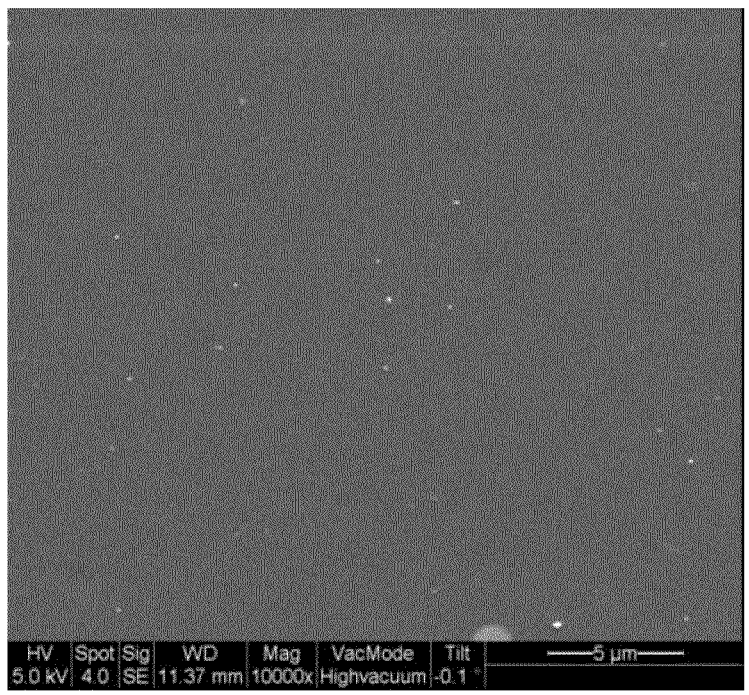
FIGS. 3A and 3B are photographs showing a side by side comparison of exemplary non-porous and porous base plates of substrates of test card assemblies taken using a scanning electron microscope.
Figure 3B:
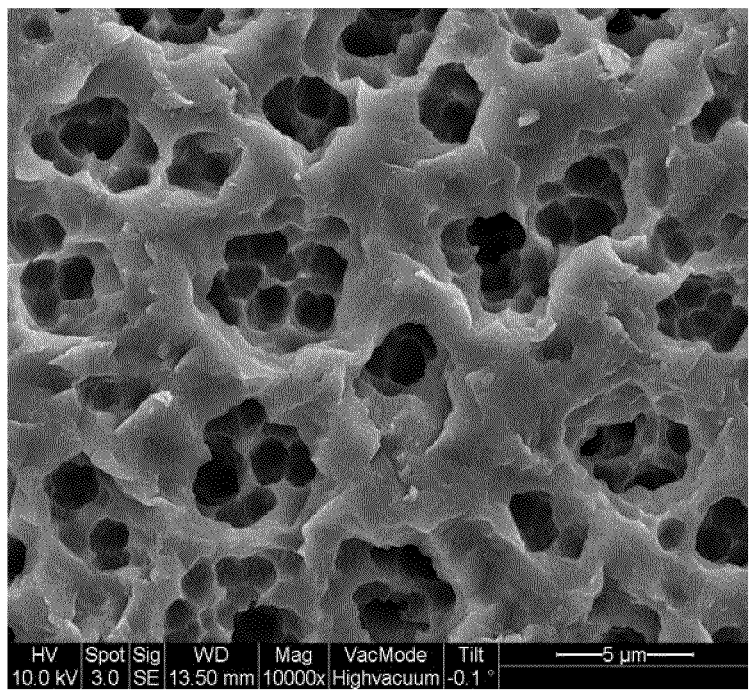

FIGS. 3A and 3B are photographs showing a side by side comparison of exemplary non-porous and porous base plates of test card assemblies taken using a scanning electron microscope. In FIG. 3B, the diameter of pore size of the base plate is in a range of about 0.1 µm to about 10 µm with an average diameter of about 3.39 µm. Pore distribution on the base plate is about $5.04 \times 10^6$ holes/cm$^2$.

Figure 4:
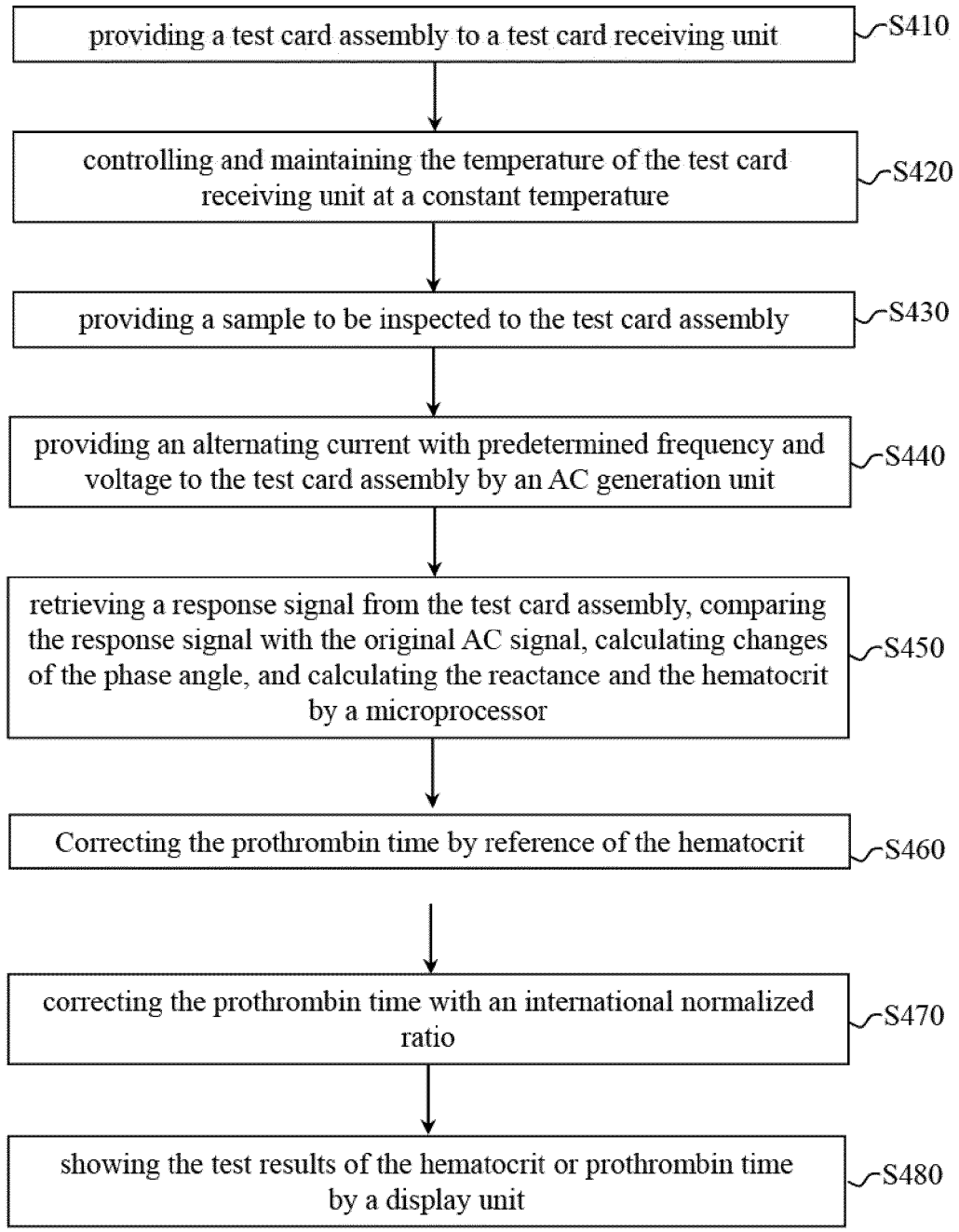
FIG. 4 is a flowchart schematically illustrating one embodiment of the diagnostic method for determining HCT and PT according to the present invention.

FIG. 4 is a flowchart schematically illustrating one embodiment of a diagnostic method for determining HCT and prothrombin time according to the present invention. The method for measuring HCT and prothrombin time in FIG. 4 includes at least these steps: providing a test card assembly to a test card receiving unit (S410); controlling and maintaining the temperature of the test card receiving unit at a constant temperature (S420); providing a sample to be inspected to the test card assembly (S430); providing an alternating current with predetermined frequency and voltage to the test card assembly by an AC generation unit (S430); sensing a response signal from the test card assembly and determining a change in the phase of the signals (i.e., phase shift) and calculating the reactance and the HCT using a microprocessor (S450); correcting the prothrombin time by reference of the HCT (S460); correcting the prothrombin time with an international normalized ratio (S470); and providing inspected results to a display unit (S480).

According to one embodiment of the present invention, the response signal retrieved from the test card is digitized and converted by the discrete fourier transform (DFT) by a microprocessor. Thus, as known to those skilled in the art, the real value and imaginary value may be determined by the method shown below:

$$X(k) = DFT[x(n)] = \sum_{n=0}^{N-1} x(n) W_N^{kn},\ 0 \le k \le N-1, \quad (1)$$

$$W_N = e^{-j\frac{2\pi}{N}} \quad (2)$$

where X(k) is fourier value of digital signal, x(n) is original value of digital signal, n is current point of digital signal, and N is total number of digital signal. Further, the phase may be calculated by the imaginary value and real value according to the following formula:

$$\text{Phase} = \tan^{-1}(Im/Re) \quad (3)$$

where Im is the imaginary value (i.e., due to the reactance) and Re is the real value (i.e., due to the real resistance). As shown in the formula (3), the phase will shift by the change in the reactance in the sample.

In some embodiments, the step of determining phase change in S450 (i.e., phase change due to reactance) as discussed above includes the steps of: calculating the magnitude of impedance from the measured response signal and the applied voltage; calculating a change in the phase; calculating reactance from the change in the phase. As will be appreciated, since the alternating current has a constant frequency, the change in the phase angle is primarily due to the change in capacitance in the sample as described above. Since any changes in capacitance in the sample creates a change in the reactance portion of impedance, the change in reactance may be used to yield accurate HCT and PT values as discussed below and shown on the attached Figures.

From the measured reactance the HCT can be calculated by interpolation. One example of calculating the HCT is described below. A traditional method of using the impedance in calculating the HCT is also described as a comparison.

Figure 5:
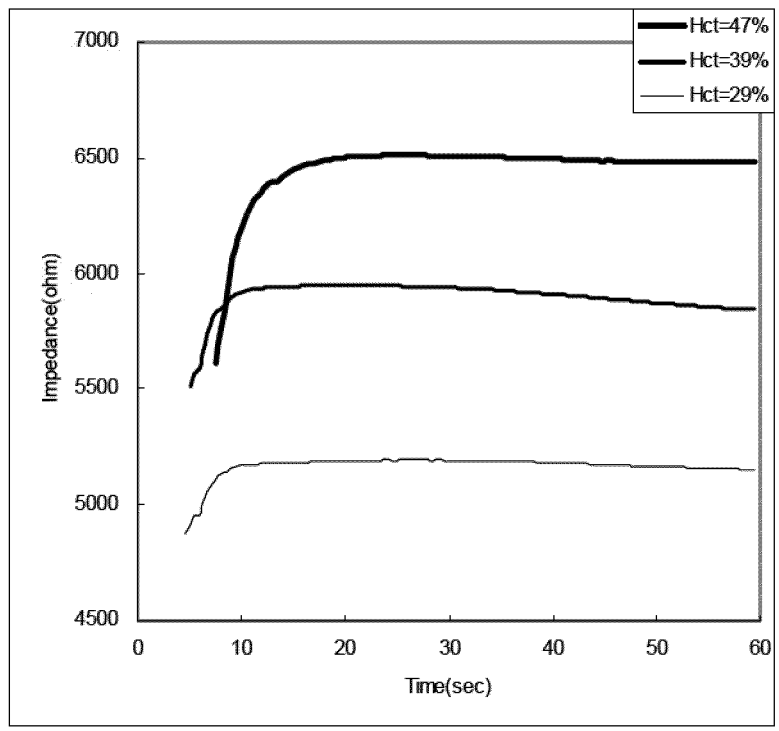
FIG. 5 is experimental graph showing the change of impedance vs. coagulation time in seconds, which illustrates a change in slope as a whole blood sample coagulates by a typical impedance measurement method.
Figure 6:
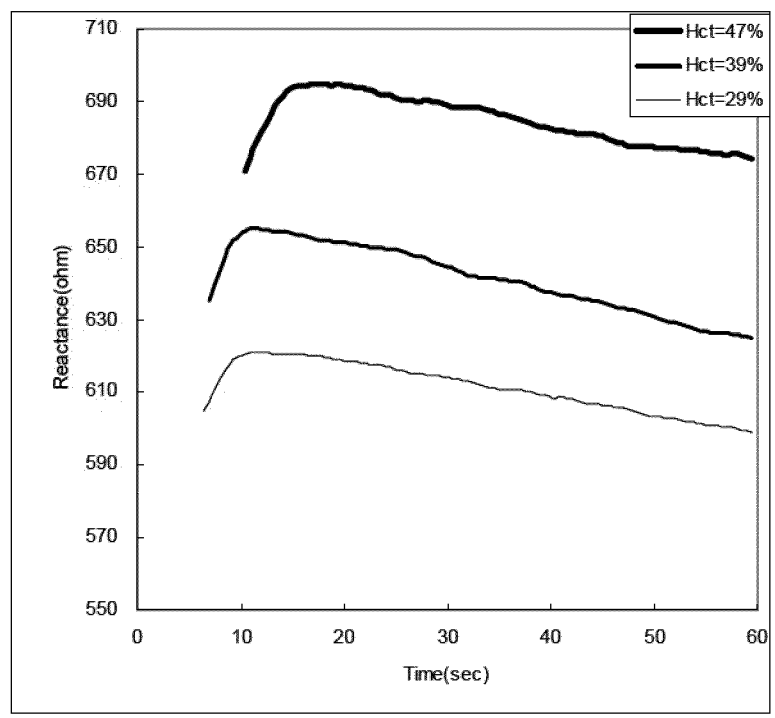
FIG. 6 is experimental graph showing the change of reactance vs. coagulation time in seconds, which illustrates a change in slope as a whole blood sample coagulates by the reactance measurement method.
Figure 7:
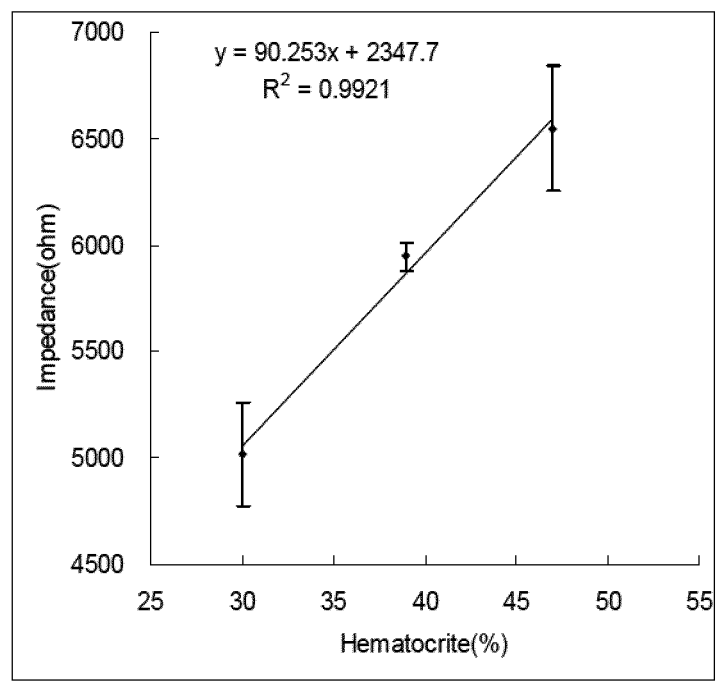
FIGS. 7 and 8 are the relation of HCT and impedance (FIG. 7) and HCT and reactance (FIG. 8) calculated from the experimental graphs of FIGS. 5 and 6, respectively.

FIGS. 5 and 6 depict experimental graphs showing the impedance and reactance increase with higher percentage HCT, respectively. As shown in the graph in FIG. 6, in this particular example, in the 11th second, the reactance of different HCT (29, 39 and 47%) was respectively 620.29, 652.17 and 676.59 ohm. Then, the relation of HCT and impedance (FIG. 7) or HCT and reactance (FIG. 8) were calculated. As shown in FIG. 5, in this particular example, the optimal impedance sampling time of HCT was at about 20 seconds or more, and Impedance vs. HCT calibration curve has an equation of y=90.253x+2347.7. Further, as shown in FIG. 6, the optimal reactance sampling time of HCT was at about 11 seconds or more, and Reactance vs. HCT calibration curve had an equation of y=3.1304x+529.68. As will be appreciated, x is the HCT, and y is the impedance or reactance, respectively.

FIGS. 9 and 10 depict exemplary impedance and reactance values measured by an LCR meter every 0.5 second over 60 seconds. In one example, whole blood was collected from a subject, and various samples were prepared by adding different amounts of anticoagulant drug (heparin) to the collected whole blood. In one instance, the concentration of heparin used to modulate the coagulation time (PT) was between about 1 U and about 30 U per milliliter. Then, the blood samples with different PT were analyzed to measure the impedance or reactance by a LCR meter (Hioki Model No. 3532-50).

Figure 8:
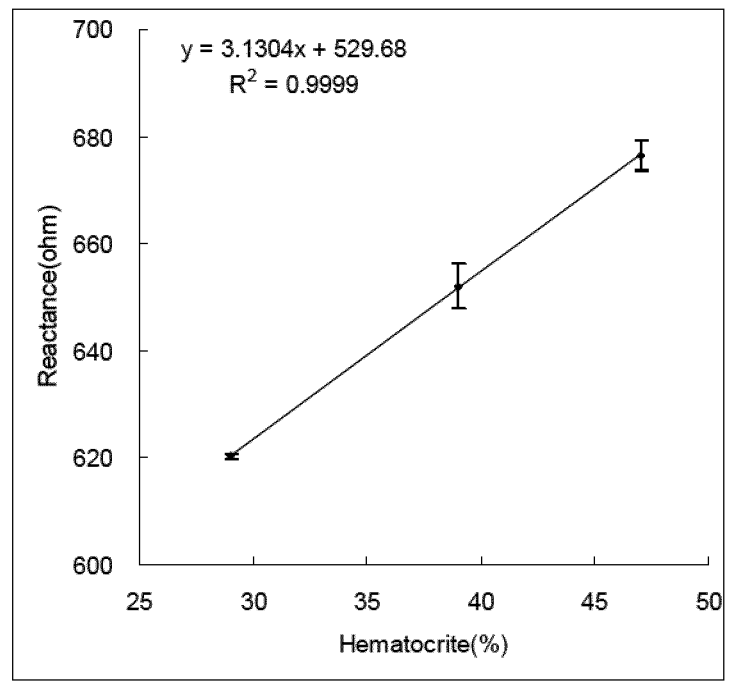

FIGS. 11 and 12 depict an exemplary PT vs. impedance change rate calibration curve and an exemplary PT vs. reactance change rate calibration curve, respectively. In this particular example, the impedance or reactance change rate was computed every 10 sec by the LCR meter. For example, the change rate from 30 second to 40 second was computed by following formula: Impedance change rate 30 to 40=$(Z_{40}-Z_{30})/(Time_{40}-Time_{30})$, wherein Z is impedance, and Reactance change rate 30 to 40=$(X_{40}-X_{30})/(Time_{40}-Time_{30})$, wherein X is reactance. The computation step was repeated to compute the impedance or reactance change rate of the blood for samples with different PTs, and thereby determine the PT vs. impedance change rate calibration curve (FIG. 7) and the PT vs. reactance change rate calibration curve (FIG. 8). The PT vs. impedance change rate calibration curve had an equation of y=−0.1849x+4.562, and the PT vs. reactance change rate calibration curve had an equation of y=−0.0256x+0.3604. As will be appreciated, x is the real PT, and y is the impedance or reactance change rate.

As shown in FIGS. 11 and 12, the diagnostic results of the reactance measurement method (FIG. 12) showed a superior standard deviation (SD value) compared to the results from the typical impedance measurement method (FIG. 11). Specifically, adoption of the reactance measurement according to the present invention is advantageous compared to the typical impedance measurement method in that the standard deviation in the reactance measurement is significantly reduced and the linear regression value (R2) in this example is about 0.9986. Accordingly, the reactance measurement method according to the present invention yields a more accurate result than the traditional impedance measurement method, and the slope deviation is acceptable even as blood coagulation process is extended, thus easily adjusting the values.

On the other hand, in this particular example, the linear regression ($R^2$) for the PT vs. impedance change rate calibration curve was about 0.939 as shown in FIG. 11. Accordingly, the impedance method is more likely to cause an inaccurate measurement.

In the above example, the impedance and reactance of a blood sample were measured by the LCR meter, and its impedance change rate and reactance change rate were calculated. Specifically, the HCT was calculated by using the HCT calibration curve with the formula, HCT=(impedance−2347.7)/90.253 or HCT=(reactance−529.68)/3.1304. Then, the real PT is calculated by the PT calibration curve. Different HCT may correspond with different PT calibration curve. In this particular example, the PT was calculated by using the PT calibration curve with the formula, PT=(impedance change rate−4.562)/−0.1849 or PT=(reactance change rate−0.3604)/−0.0256.

FIGS. 13 and 14 depict exemplary graphs of Calibrated PT vs. Real PT by impedance and Calibrated PT vs. Real PT by reactance, respectively. The PT values computed by the calibration curve and the real PT values measured by the automated blood coagulation analyzer (Sysmex CA-500 series) were compared.

The increase or decrease in the HCT influences blood clotting time (PT) and the impendence or reactance change rate value. Specifically, a higher HCT causes the impendence or reactance change rate value to increase. Hence, the PT determination process in some embodiments may include an HCT correction step. A device according to some embodiments of the present invention includes an internal memory for storing experimental results of PT values for different HCT samples that can be used to correct PT by reference of the HCT. For example, a data base may be built up in the meter that includes serial experiment results of real PT values for different HCT samples. For example, values between 30 HCT % to 60 HCT % may be stored for every 5 HCT % of real PT value. Therefore, for example, when PT value for 35% HCT ($PT_1$) and PT value for 40% HCT ($PT_2$) are stored in the memory, a $PT_3$ value for 38% HCT can be estimated to be $(PT_1 \times 2/5)+(PT_2 \times 3/5)$.

In one aspect of the invention, the PT values may be corrected with an international normalized ratio shown in the following formula:

$$INR = \left(\frac{\text{Patient } PT}{\text{Mean } PT}\right)^{ISI} \quad (4)$$

where INR is international normalized ratio, PT is prothrombin time, and ISI is an international sensitivity index.

FIGS. 15A and 15B are experimental graphs showing the blood coagulation analyses using a porous substrate and a non-porous substrate for the test card, respectively. As illustrated in the Figures, the analyses employing a porous substrate provided superior results.

FIGS. 16A-16C depict experimental graphs showing the blood coagulation analyses at different frequencies by the reactance measurement according to the present invention. Coagulation times between 15-50 seconds is measured for the blood samples at frequencies of 0.1 kHz, 10 kHz and 50 kHz, and test results $R^2$ were obtained by calculating regression analysis of 0.9636, 0.9923, and 0.9858 respectively. In this case, the regression analysis indicates that using frequencies of 10 KHz and 50 KHz provide greater accuracy as compared to a frequency of 0.1 KHz.

While the invention has been described by way of examples and in terms of preferred embodiments, it would be apparent to those skilled in the art to make various equivalent replacements, amendments and modifications in view of specification of the invention. Therefore, the scope of the appended claims should be accorded the broadest interpretation so as to encompass all such replacements, amendments and modifications without departing from the spirit and scope of the invention.

The invention claimed is:

1. A diagnostic device for measuring hematocrit (HCT) or prothrombin time (PT) of a sample, comprising:
   a sensor device; and
   a test card assembly including one or more pairs of electrodes,
   wherein the sensor device comprises
   a test card receiving unit for accommodating the test card assembly;
   a power source for providing an AC test signal at a constant frequency to electrodes of the test card assembly;
   a signal retrieving unit coupled to the test card assembly;
   a microprocessor in the sensor device programmed for (i) performing a reactance analysis of a sample provided on the test card assembly by comparing the AC test signal and a response signal from the test card assembly in response to the AC test signal, calculating a change in phase of the AC test signal, and calculating a reactance from the change in phase of the AC test signal, and (ii) determining PT or HCT of the sample; and, a display for displaying the PT or HCT of the sample.

2. The diagnostic device as claimed in claim 1, wherein the reactance analysis further comprises:

calculating a reactance due to a change in capacitance, and transforming the change in capacitance with algorithms and correcting to the prothrombin time by reference of the HCT.

3. The diagnostic device as claimed in claim 1, the reactance analysis further comprises correcting the PT with an international normalized ratio.

4. The diagnostic device as claimed in claim 1, wherein the test card assembly comprises one or more pairs of the noble metal electrodes, set on the same plane.

5. The diagnostic device as claimed in claim 1, wherein the test card assembly comprises one or more pairs of the electrodes, set on different planes.

6. The diagnostic device as claimed in claim 1, wherein the test card assembly comprises a base plate comprising a porous material that includes holes, voids or cavities thereon.

7. The diagnostic device as claimed in claim 6, wherein the base plate of the test card assembly comprises pores such as holes, voids or cavities thereon, with diameters approximately in a range of about 0.1 μm to about 10 μm.

8. The diagnostic device as claimed in claim 7, wherein the microprocessor further transforms the capacitance with algorithms, corrects to the PT by reference of the HCT; and calculates the PT with an international normalized ratio.

* * * * *